(12) United States Patent
Gebreselassie et al.

(10) Patent No.: US 7,641,892 B2
(45) Date of Patent: *Jan. 5, 2010

(54) TOOTH WHITENING COMPOSITIONS AND DELIVERY SYSTEMS THEREFOR

(75) Inventors: Petros Gebreselassie, Piscataway, NJ (US); Navroz Boghani, Flanders, NJ (US)

(73) Assignee: Cadburry Adams USA, LLC, Parsippany, NJ (US)

( * ) Notice: Subject to any disclaimer, the term of this patent is extended or adjusted under 35 U.S.C. 154(b) by 47 days.

This patent is subject to a terminal disclaimer.

(21) Appl. No.: 10/901,511

(22) Filed: Jul. 29, 2004

(65) Prior Publication Data
US 2006/0024244 A1   Feb. 2, 2006

(51) Int. Cl.
*A23G 4/00*   (2006.01)
*A61K 9/68*   (2006.01)
*A61K 8/00*   (2006.01)
*A61Q 11/00*  (2006.01)

(52) U.S. Cl. .......................... 424/48; 424/49; 424/400; 426/3; 426/5

(58) Field of Classification Search .................. 424/48, 424/49
See application file for complete search history.

(56) References Cited

U.S. PATENT DOCUMENTS

| | | | |
|---|---|---|---|
| 1,633,336 A | 6/1927 | Larson | |
| 1,936,456 A | 11/1933 | Larson et al. | |
| 2,191,199 A | 2/1940 | Hall | |
| 2,197,719 A | 4/1940 | Conner | |
| 2,876,167 A | 3/1959 | Manahan | |
| 2,886,446 A | 5/1959 | Kramer et al. | |
| 3,004,897 A | 10/1961 | Shore | |
| 3,052,552 A | 9/1962 | Koerner et al. | |
| 3,117,027 A | 1/1964 | Lindlof et al. | |
| 3,124,459 A | 3/1964 | Erwin | |
| 3,241,520 A | 3/1966 | Wurster et al. | |
| 3,475,533 A | 10/1969 | Mayrand | |
| 3,538,230 A | 11/1970 | Pader et al. | |
| 3,664,962 A | 5/1972 | Kelly et al. | |
| 3,664,963 A | 5/1972 | Pasin | |
| 3,677,771 A | 7/1972 | Kolar, Jr. | |
| 3,795,744 A | 3/1974 | Ogawa et al. | |
| 3,821,417 A | 6/1974 | Westall et al. | |
| 3,826,847 A | 7/1974 | Ogawa et al. | |
| 3,857,964 A | 12/1974 | Yolles | |
| 3,862,307 A | 1/1975 | Di Guilio | |
| 3,872,021 A | 3/1975 | McKnight | |
| 3,878,938 A | 4/1975 | Venables et al. | |
| 3,912,817 A | 10/1975 | Sapsowitz | |
| 3,943,258 A | 3/1976 | Bahoshy et al. | |
| 3,962,416 A | 6/1976 | Katzen | |
| 3,992,519 A | 11/1976 | Hofmann et al. | |
| 4,037,000 A | 7/1977 | Burge et al. | |
| 4,083,995 A | 4/1978 | Mitchell et al. | |
| 4,107,360 A | 8/1978 | Schmidgall | |
| 4,130,638 A | 12/1978 | Dhabhar et al. | |
| 4,138,477 A * | 2/1979 | Gaffar | 424/52 |
| 4,148,872 A | 4/1979 | Wagenknecht et al. | |
| 4,150,112 A | 4/1979 | Wagenknecht et al. | |
| 4,156,715 A | 5/1979 | Wagenknecht et al. | |
| 4,156,716 A | 5/1979 | Wagenknecht et al. | |
| 4,157,385 A | 6/1979 | Wagenknecht et al. | |
| 4,159,315 A | 6/1979 | Wagenknecht et al. | |
| 4,160,054 A | 7/1979 | Wagenknecht et al. | |
| 4,160,820 A | 7/1979 | Wagenknecht et al. | |
| 4,183,914 A * | 1/1980 | Gaffar et al. | 424/48 |
| 4,208,431 A | 6/1980 | Friello et al. | |
| 4,217,368 A | 8/1980 | Witzel et al. | |
| 4,224,345 A | 9/1980 | Tezuka et al. | |
| 4,271,199 A | 6/1981 | Cherukuri et al. | |
| 4,295,845 A | 10/1981 | Sepulveda et al. | |
| 4,314,990 A | 2/1982 | Denny, Jr. et al. | |
| 4,340,583 A | 7/1982 | Wason | |
| 4,352,825 A | 10/1982 | Cherukuri et al. | |
| 4,363,756 A | 12/1982 | Sepulveda et al. | |
| 4,367,219 A | 1/1983 | Schole | |
| 4,384,004 A | 5/1983 | Cea et al. | |
| 4,452,821 A | 6/1984 | Gergely | |
| 4,457,857 A | 7/1984 | Sepulveda et al. | |

(Continued)

FOREIGN PATENT DOCUMENTS

EP   0 067 595   12/1982

(Continued)

OTHER PUBLICATIONS

Green, S. A. DDS, Plaque and Calculus, http://www.qualitydentistry.com/dental/ecare/pandc.html pp. 1-2, 2004.*
Prencipe et al.; Squeezing out a better toothpaste; Chemtech, Dec. 1995;http://pubs.acs.org/hotartcl/chemtech/95/dec/dec.html; printed Apr. 20, 2004; pp. 1-7.
Gantrez® AN; ISP Polymers for Oral Care; http://www.ispcorp.com/products/oralcare/content/brochure/oral/prod.html, printed Jun. 9, 2004, pp. 1-5.
Demmers et al.; Effect of Surfactants and Proteolytic Enzymes on Artificial Calculus Formation; Surfactants and Enzymes: Calculus; pp. 28-35.
Demmers et al; Effect of Surfactants and Proteolytic Enzymes on Artificial Calculus Formation; Journal of Periodontology, American Academy of Periodontology, Illinois, US; vol. 38, No. 4; 1967, pp. 294-301.

*Primary Examiner*—Frederick Krass
*Assistant Examiner*—Lezah W Roberts
(74) *Attorney, Agent, or Firm*—Hoffmann & Baron, LLP

(57) ABSTRACT

Stain-removing oral compositions, such as gum compositions are herein provided. The compositions include an orally acceptable carrier and a stain-removing anionic surfactant. The surfactant includes a fatty acid salt having at least one hydroxyl functionality. The fatty acid salt may be a salt of ricinoleic acid, and may be combined with a chelating agent and/or an abrasive. The chelating agent may be a polyphosphate and the abrasive may be a silica abrasive.

53 Claims, No Drawings

U.S. PATENT DOCUMENTS

| | | |
|---|---|---|
| 4,485,118 A | 11/1984 | Carroll et al. |
| 4,513,012 A | 4/1985 | Carroll et al. |
| 4,585,649 A | 4/1986 | Lynch |
| 4,590,075 A | 5/1986 | Wei et al. |
| 4,597,970 A | 7/1986 | Sharma et al. |
| 4,614,649 A | 9/1986 | Gorman et al. |
| 4,673,577 A | 6/1987 | Patel |
| 4,722,845 A | 2/1988 | Cherukuri et al. |
| 4,726,953 A | 2/1988 | Carroll et al. |
| 4,740,376 A | 4/1988 | Yang |
| 4,749,575 A | 6/1988 | Rotman |
| 4,751,095 A | 6/1988 | Karl et al. |
| 4,752,481 A | 6/1988 | Dokuzovic |
| 4,753,790 A | 6/1988 | Silva et al. |
| 4,771,784 A | 9/1988 | Kozin et al. |
| 4,800,087 A | 1/1989 | Mehta |
| 4,804,548 A | 2/1989 | Sharma et al. |
| 4,816,265 A | 3/1989 | Cherukuri et al. |
| 4,822,599 A | 4/1989 | Mitra |
| 4,828,845 A | 5/1989 | Zamudio-Tena et al. |
| 4,828,857 A | 5/1989 | Sharma et al. |
| 4,842,762 A | 6/1989 | Sabol, Jr. et al. |
| 4,911,934 A | 3/1990 | Yang et al. |
| 4,915,958 A | 4/1990 | Faust et al. |
| 4,918,182 A | 4/1990 | Jackson et al. |
| 4,919,841 A | 4/1990 | Kamel et al. |
| 4,923,684 A | 5/1990 | Ibrahim et al. |
| 4,927,646 A | 5/1990 | Jenner et al. |
| 4,929,447 A | 5/1990 | Yang |
| 4,931,293 A | 6/1990 | Cherukuri et al. |
| 4,933,190 A | 6/1990 | Cherukuri et al. |
| 4,952,407 A | 8/1990 | Record et al. |
| 4,971,797 A | 11/1990 | Cherukuri et al. |
| 4,978,537 A | 12/1990 | Song |
| 4,985,236 A | 1/1991 | Ibrahim et al. |
| 4,997,659 A | 3/1991 | Yatka et al. |
| 5,009,900 A | 4/1991 | Levine et al. |
| 5,011,830 A * | 4/1991 | Leonard et al. ............... 424/57 |
| 5,017,385 A | 5/1991 | Wienecke |
| 5,043,154 A | 8/1991 | Gaffar et al. |
| 5,043,169 A | 8/1991 | Cherukuri et al. |
| 5,057,327 A | 10/1991 | Yatka et al. |
| 5,057,328 A | 10/1991 | Cherukuri et al. |
| 5,059,429 A | 10/1991 | Cherukuri et al. |
| 5,064,658 A | 11/1991 | Cherukuri et al. |
| 5,073,389 A | 12/1991 | Weinecke |
| 5,080,887 A | 1/1992 | Gaffar et al. |
| 5,082,671 A | 1/1992 | Cherukuri |
| 5,084,278 A | 1/1992 | Mehta |
| 5,096,699 A | 3/1992 | Gaffar et al. |
| 5,096,701 A | 3/1992 | White, Jr. et al. |
| 5,100,678 A | 3/1992 | Reed et al. |
| 5,108,763 A | 4/1992 | Chau et al. |
| 5,126,151 A | 6/1992 | Bodor et al. |
| 5,139,793 A | 8/1992 | Johnson et al. |
| 5,139,794 A | 8/1992 | Patel et al. |
| 5,139,798 A | 8/1992 | Yatka et al. |
| 5,154,939 A | 10/1992 | Broderick et al. |
| 5,164,210 A | 11/1992 | Campbell et al. |
| 5,169,657 A | 12/1992 | Yatka et al. |
| 5,169,658 A | 12/1992 | Yatka et al. |
| 5,174,514 A | 12/1992 | Prodi |
| 5,176,900 A | 1/1993 | White, Jr. et al. |
| 5,180,578 A * | 1/1993 | Gaffar et al. ............... 424/52 |
| 5,198,251 A | 3/1993 | Song et al. |
| 5,202,112 A | 4/1993 | Prencipe et al. |
| 5,208,009 A | 5/1993 | Gaffar et al. |
| 5,227,182 A | 7/1993 | Song et al. |
| 5,229,148 A | 7/1993 | Copper |
| 5,240,710 A | 8/1993 | Bar-Shalom et al. |
| 5,256,402 A | 10/1993 | Prencipe et al. |
| 5,273,741 A | 12/1993 | Gaftar et al. |
| 5,300,283 A | 4/1994 | Prencipe et al. |
| 5,334,375 A | 8/1994 | Nabi et al. |
| 5,336,509 A | 8/1994 | McGrew et al. |
| 5,352,439 A | 10/1994 | Norfleet et al. |
| 5,380,530 A | 1/1995 | Hill |
| 5,385,729 A | 1/1995 | Prencipe et al. |
| 5,391,315 A | 2/1995 | Ashkin |
| 5,413,799 A | 5/1995 | Song et al. |
| 5,415,880 A | 5/1995 | Song et al. |
| 5,437,876 A | 8/1995 | Synosky et al. |
| 5,462,754 A | 10/1995 | Synosky et al. |
| 5,498,378 A | 3/1996 | Tsaur et al. |
| 5,501,864 A | 3/1996 | Song et al. |
| 5,503,823 A | 4/1996 | Norfleet et al. |
| 5,505,933 A | 4/1996 | Norfleet et al. |
| 5,532,004 A | 7/1996 | Bell et al. |
| 5,554,380 A * | 9/1996 | Cuca et al. ................. 424/441 |
| 5,582,816 A | 12/1996 | Mandanas et al. |
| 5,589,160 A | 12/1996 | Rice |
| 5,599,527 A | 2/1997 | Hsu et al. |
| 5,603,920 A | 2/1997 | Rice |
| 5,618,517 A | 4/1997 | Miskewitz |
| 5,629,011 A * | 5/1997 | Illum ....................... 424/434 |
| 5,629,035 A | 5/1997 | Miskewitz |
| 5,645,821 A | 7/1997 | Libin |
| 5,651,958 A | 7/1997 | Rice |
| 5,658,553 A | 8/1997 | Rice |
| 5,676,932 A | 10/1997 | Wason et al. |
| 5,698,215 A | 12/1997 | Kalili et al. |
| 5,702,687 A | 12/1997 | Miskewitz |
| 5,713,738 A | 2/1998 | Yarborough |
| 5,716,601 A | 2/1998 | Rice |
| 5,736,175 A | 4/1998 | Cea et al. |
| 5,756,074 A | 5/1998 | Ascione et al. |
| 5,789,002 A | 8/1998 | Duggan et al. |
| 5,800,848 A | 9/1998 | Yatka et al. |
| 5,824,291 A | 10/1998 | Howard |
| 5,869,028 A | 2/1999 | McGill et al. |
| 5,879,728 A | 3/1999 | Graff et al. |
| 5,912,007 A | 6/1999 | Pan et al. |
| 5,939,051 A | 8/1999 | Santalucia et al. |
| 6,056,992 A | 5/2000 | Lew |
| 6,190,644 B1 | 2/2001 | McClanahan et al. |
| 6,238,690 B1 | 5/2001 | Kiefer et al. |
| 6,261,540 B1 | 7/2001 | Nelson |
| 6,290,933 B1 | 9/2001 | Durga et al. |
| 6,365,209 B2 | 4/2002 | Cherukuri |
| 6,379,654 B1 | 4/2002 | Gebreselassie et al. |
| 6,416,744 B1 | 7/2002 | Robinson et al. |
| 6,428,827 B1 | 8/2002 | Song et al. |
| 6,471,945 B2 | 10/2002 | Luo et al. |
| 6,475,469 B1 | 11/2002 | Montgomery |
| 6,479,071 B2 | 11/2002 | Holme et al. |
| 6,485,739 B2 | 11/2002 | Luo et al. |
| 6,506,366 B1 | 1/2003 | Leinen et al. |
| 6,534,091 B1 | 3/2003 | Garces Garces et al. |
| 6,555,145 B1 | 4/2003 | Cherukuri |
| 6,685,916 B1 * | 2/2004 | Holme et al. ................. 424/48 |
| 6,692,778 B2 | 2/2004 | Yatka et al. |
| 6,696,044 B2 | 2/2004 | Luo et al. |
| 6,759,066 B2 | 7/2004 | Schnell et al. |
| 7,022,314 B2 | 4/2006 | Barabolak et al. |
| 2001/0043907 A1 | 11/2001 | Luo et al. |
| 2002/0044968 A1 | 4/2002 | van Lengerich |
| 2002/0150616 A1 | 10/2002 | Vandecruys |
| 2003/0055105 A1* | 3/2003 | Ito et al. ..................... 514/473 |
| 2003/0099740 A1 | 5/2003 | Colle et al. |
| 2003/0113274 A1 | 6/2003 | Holme et al. |
| 2003/0133896 A1* | 7/2003 | Dietz et al. ............. 424/70.14 |
| 2004/0136928 A1 | 7/2004 | Holme et al. |

| | | | |
|---|---|---|---|
| 2005/0025721 A1 | 2/2005 | Holme et al. | |

FOREIGN PATENT DOCUMENTS

| | | |
|---|---|---|
| EP | 0 252 374 | 1/1988 |
| EP | 0 255 260 | 2/1988 |
| EP | 0 434 321 | 6/1991 |
| EP | 0 453 397 | 10/1991 |
| GB | 22111 | 2/1903 |
| GB | 753979 | 8/1956 |
| GB | 2309386 | 5/1996 |
| JP | 1-206969 | 8/1989 |
| JP | 2-83030 | 3/1990 |
| WO | WO 88/00463 | 1/1988 |
| WO | WO 92/06160 | 4/1992 |
| WO | WO 95/33034 | 12/1995 |
| WO | WO 96/19193 | 6/1996 |
| WO | WO 97/02009 | 1/1997 |
| WO | WO 97/02011 | 1/1997 |
| WO | WO 98/03076 | 1/1998 |
| WO | WO 98/18339 | 5/1998 |
| WO | WO 98/23165 | 6/1998 |
| WO | WO 98/29088 | 7/1998 |
| WO | WO 99/27798 | 6/1999 |
| WO | WO 99/43294 | 9/1999 |
| WO | WO 00/35296 | 6/2000 |
| WO | WO 00/35298 | 6/2000 |
| WO | WO 00/75274 | 12/2000 |
| WO | WO 02/055649 | 7/2002 |
| WO | WO 03/020047 | 3/2003 |
| WO | WO 03/039503 | 5/2003 |
| WO | WO 2005/013712 | 2/2005 |
| WO | WO 2005/051427 | 6/2005 |

* cited by examiner

TOOTH WHITENING COMPOSITIONS AND DELIVERY SYSTEMS THEREFOR

FIELD

The present invention is generally directed to oral compositions containing an effective amount of a stain-removing anionic surfactant. In particular, the invention is directed to oral compositions including a fatty acid salt having at least one hydroxyl functionality.

BACKGROUND

Unblemished white teeth have long been considered cosmetically desirable. Unfortunately, in the absence of thorough dental cleaning, teeth can become discolored or stained from color-causing substances present in food, beverages, tobacco, and the like, and internal sources such as blood, amalgam-based fillings, and antibiotics (e.g., tetracycline).

The tooth structures that are generally responsible for presenting a stained appearance are enamel, dentin, and the acquired pellicle. Tooth enamel is predominately formed from inorganic material, mostly in the form of hydroxyapatite crystals, and further contain approximately 5% organic material primarily in the form of collagen. In contrast, dentin is composed of about 20% protein including collagen, the balance existing of inorganic material, predominately hydroxyapatite crystals, similar to that found in enamel. The acquired pellicle is a proteinaceous layer present on the surface of tooth enamel which reforms rapidly after an intensive tooth cleaning.

Discoloration of teeth can result from extrinsic and/or intrinsic staining. Extrinsic staining of the acquired pellicle can arise as a result of compounds, such as tannins and other polyphenolic compounds, that have become trapped in and tightly bound to the proteinaceous layer on the surface of the teeth. Discoloration from this type of staining can usually be removed by mechanical methods of tooth cleaning. In contrast, intrinsic staining occurs when the staining compounds penetrate the enamel and even the dentin, or alternatively, such staining arises from sources within the tooth. Discoloration from intrinsic staining is not readily amenable to mechanical methods of tooth cleaning. Chemical methods, which utilize substances that can penetrate into the tooth structure, are usually required to eliminate such discoloration.

Currently, there are a number of methods for removing stains in teeth. These methods are generally based on the use of abrasives, hydrolytic agents or oxidizing agents to break down the staining material. For example, mechanical methods of tooth cleaning are known whereby the stain is mechanically abraded through the use of abrasives or polishing agents normally employed in toothpaste preparations. Typical preparations containing abrasives are toothpastes, gels or powder dentifrices, which require close contact with the teeth. Brushing and similar scrubbing or polishing action is typically required as a compliment to successful stain removal. Typical abrasives include hydrated silica, calcium carbonate, sodium bicarbonate and alumina.

Hydrolytic agents including proteolytic enzymes can also be used to whiten teeth. These products are usually in the form of pastes or gels, and function to whiten teeth by removing the plaque and calculus that have been entrapped the stain.

Oxidizing agents such as urea peroxide, hydrogen peroxide or calcium peroxide, represent the most common forms of whitening agents for tooth enamels. It is believed that peroxides whiten teeth by releasing hydroxyl radicals capable of breaking down the plaque/stain complex into a form that can be flushed away or removed by an abrasive.

Other active stain-removing components include surface-active agents, such as anionic surfactants and chelators, which have been incorporated into stain-removing compositions because of their stain-removing properties. For example, anionic surfactants typically employed in dentifrice compositions include sodium lauryl sulfate and sodium N-lauryl sarcosinate. Furthermore, chelators, such as polyphosphates, are typically employed in dentifrice compositions as tartar control ingredients. For example, tetrasodium pyrophosphate and sodium tri-polyphosphate are typical ingredients found in such compositions.

Unlike toothpaste, mouthwash and other dentifrice compositions, gum compositions present unique problems in delivering agents. Chewing gum compositions typically comprise a water-insoluble gum base which provides the bulk to the gum composition, but which invariably traps agents having compatibility with the gum base. Adding additional amounts of an agent is problematical because the same can have an adverse affect on the integrity, sensory and/or taste properties of the gum composition.

Stain-removing gum compositions are known. For example, gum compositions including sodium tripolyphosphate and xylitol are known. Also, gum compositions are known, which include hexametaphosphate and an abrasive silica material. Moreover, a dental gum is known, which includes the following ingredients: sodium tripolyphosphate, tetrasodium pyrophosphate, a silica abrasive and zinc acetate. A whitening gum composition is also known, which includes the abrasives sodium bicarbonate and calcium carbonate, and is sold under the brand name V6®.

U.S. Pat. No. 5,603,920 to Rice discloses a dentifrice composition that may be used in the form of a gum. The dentifrice composition includes a silica abrasive, a chelating agent (disclosed as including a pyrophosphate salt) and a surfactant. The surfactant is disclosed as preferably being selected from sarcosinate surfactants, isethionate surfactants and taurate surfactants. Exemplified surfactants are sodium lauryl sarcosinate and sodium lauryl sulfate.

Stain-removing gum compositions are known including anionic surfactants such as fatty acid salts (see U.S. Pat. Nos. 6,471,945, 6,479,071 and 6,696,044). For example, sodium stearate is a fatty acid salt employed in a gum product sold under the brand name Trident White®. Sodium stearate is a surfactant containing both hydrophilic and lipophilic groups. This fatty acid salt is known to solubilize stains into saliva and to loosen the stain so that they can be easily removed by brushing or salvia. It is also known to enter and break up the continuous plaque matrix, and to prevent stain build-up by interfering with the calcium bridge formation between plaque and food product. Encapsulating sodium stearate in sugar alcohols, and only loosely containing sodium stearate within the gum composition, can facilitate its release from the gum base.

It would be beneficial to provide further gum compositions for cleaning teeth, which employ a stain-removing agent that can be both effectively incorporated into a chewing gum composition and released therefrom during chewing in a manner that provides an effective amount of the stain-removing agent(s). In particular, it would be advantageous to provide oral compositions, such as chewing gums, that include a stain-removing agent(s) that can be effectively released from a variety of gum bases, has high solubility in saliva, avoids interaction with gum ingredients (e.g. lecithin) and avoids chemical changes in acidic environments, such as fruit gums.

SUMMARY OF THE INVENTION

The present invention is generally directed to stain-removing oral compositions in which a stain-removing material has been effectively incorporated therein so that a sufficient amount is available for a stain-removing effect.

In one aspect of the present invention, there is provided a stain-removing oral composition including an orally acceptable carrier and a surfactant in an effective amount to remove stains from teeth, wherein the surfactant comprises a fatty acid salt having at least one hydroxyl functionality. In some embodiments, the fatty acid salt is a salt of ricinoleic acid.

The oral compositions of this invention can include, but are not limited to, any number of compositions, including gums, confectionary compositions, toothpastes and mouthwashes. For example, certain aspects of the present invention relate to stain-removing gum compositions.

In some embodiments, the stain-removing gum composition may include a gum base and a surfactant in an effective amount to remove stains from teeth, wherein the surfactant includes a fatty acid salt having at least one hydroxyl functionality. The fatty acid salt in the stain-removing gum composition may be a salt of ricinoleic acid.

For example, in some embodiments, the invention provides a chewing gum composition including: a salt of ricinoleic acid; and a chelating agent.

Furthermore, in some embodiments, there is provided a chewing gum composition including: a gum base; and a salt of ricinoleic acid. The gum base may also include other ingredients, such as abrasives and/or chelating agents.

For example, in some embodiments, there is provided a chewing gum composition including: a gum base; a salt of ricinoleic acid; and a chelating agent.

In some embodiments, there is provided a chewing gum composition including: a gum base; a salt of ricinoleic acid; a chelating agent; and an abrasive agent.

Moreover, in some embodiments, there is provided a stain-removing gum composition including at least one ingestible fatty acid salt derived from an extract from the plant Ricinus spp, Euphorbiaceae. Ricinoleic acid is known to account for about 90% of the triglyceride fatty acids of castor oil from the seeds of this plant.

In one particular embodiment, the invention provides a chewing gum composition including: a gum base present in amounts of about 20 to about 40% by weight of the chewing gum composition; sodium ricinoleate present in amounts of about 0.05 to about 10% by weight of the chewing gum composition; silicon dioxide present in amounts of about 0.1 to about 20% by weight of the chewing gum composition; and sodium tripolyphosphate present in amounts of about 0.1 to about 5% by weight of the chewing gum composition.

Other aspects of the present invention provide methods of preparing and using the inventive stain-removing compositions herein.

In some embodiments, the invention provides a method for removing stains from teeth that includes: providing an oral composition comprising an orally acceptable carrier and a fatty acid salt having at least one hydroxyl functionality; and contacting the teeth with the provided composition for a sufficient time to remove stains from the teeth. For example, in one embodiment, stains may be removed from teeth by chewing an effective amount of a stain-removing gum composition provided herein.

Gum compositions provided herein can be prepared in any number of ways. For example, a fatty acid salt having at least one hydroxyl functionality may be combined with a gum base, or with a coating for the gum, or with both.

In some embodiments, the present invention provides a method of preparing a stain-removing gum composition that includes: heating a gum base to soften the base; mixing the softened gum base with a fatty acid salt having at least one hydroxyl functionality to obtain a substantially homogeneous mixture; cooling the mixture; and forming the cooled mixture into individual gum pieces. Other components, such as including, but not limited to, sweeteners, flavorants, fillers and colorants may also be included in the gum base, as will be described in greater detail below.

Furthermore, in some embodiments, the present invention provides a method of preparing a stain-removing gum composition, wherein the surfactant component is included within a coating for the gum. In one embodiment, the method includes first heating a gum base to soften the base; and mixing the softened gum base with at least one of the following components so as to obtain a substantially homogeneous mixture: elastomer, wax, emulsifier, bulking agent, filler, humectant, flavorant, colorant, dispersing agent, softener, plasticizer, preservative, warming agent, cooling agent, tooth whitening agent and sweetener. The method can further include cooling the mixture; forming the cooled mixture into individual gum pieces; and next coating the gum pieces with an aqueous coating solution including a fatty acid salt having at least one hydroxyl functionality. Again, in one form of the present invention, the fatty acid salt is a salt of ricinoleic acid.

DETAILED DESCRIPTION OF THE INVENTION

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the term "gum compositions" is intended to include any gum compositions, including "chewing gum" and "bubble gum."

The term "fatty acid salt" is a compound formed by replacing hydrogen in a fatty acid by a metal (or a radical that acts like a metal).

"Hydroxy fatty acid salts" as used herein are fatty acid salts having at least one hydroxyl functionality. The hydroxyl group may occur at various positions in the carbon chain which can be saturated or monoenoic. The term is intended to include salts derived from polyhydroxy fatty acids, which are most frequently produced by lipoxygenase activities.

The present invention is directed to compositions with stain-removing properties for producing a whitening effect on dental surfaces that are treated with the same. Such compositions are especially suitable for removing stains, which adhere to, or are entrapped in materials on, the surface of teeth and for preventing build-up of the stain entrapping material and stains on dental surfaces. The compositions of the present invention are meant to include products, which are not intentionally swallowed for purposes of systemic administration of therapeutic agents, but are retained in the oral cavity for a sufficient time to contact the dental surfaces for purposes of providing beneficial dental effects.

The compositions of the present invention may be in a form selected from, for example, dentifrices including mouthwashes, mouth rinses, toothpastes, tooth powders, tooth hardeners, antiplaque compositions, dental creams, dental flosses, liquids, gels, and the like; chewing gums, including center-filled gums, and the like; and confectioneries, including mints, lozenges, and the like. In some embodiments, the compositions of the present invention are in the form of chewing gums.

In accordance with the present invention, a stain-removing effective amount of a fatty acid salt having at least one hydroxyl functionality is employed in the compositions of the present invention to provide effective stain-removing activity. Applicants have discovered that fatty acid salts having at least one hydroxyl functionality improve stain-removing activity over the activity of other fatty acid salts. Moreover, relative to other fatty acid salts, Applicants have discovered that hydroxy fatty acid salts are better able to prevent build-up of stain entrapping material and stains on dental surfaces. Hydroxy fatty acid salts have a better affinity for the tooth surface, penetrate the stain/plaque faster, and bind calcium stronger because of the hydroxyl group occurring at a position in the carbon chain. This facilitates the effective removal of dental stains and allows for the formation of a film on teeth for preventing further stains. Hydroxy fatty acid salts have a greater solubility in saliva and less of an affinity for the gum base relative to other fatty acid salts. This allows it to solubilize the stain into the saliva and loosen it so that it is easily removed by brushing or saliva. Moreover, unlike other fatty acid salts, hydroxy fatty acid salts do not substantially interact with ingredients, such as lecithin, and have less of a tendency to change in acidic environments, such as those present in fruit gum. Significantly, hydroxy fatty acid salts, such as salts of ricinoleic acid, are also known to have antibacterial efficacy. For example, it is known to employ castor oil soap in a dentifrice composition in order to render mouth bacteria and their products harmless by treating them with the composition.

In some embodiments, the stain-removing oral compositions of the present invention include the combination of a hydroxy fatty acid salt and a chelating agent. Applicants have discovered that this combination of stain-removing agents improves stain-removing activity over the activity of the individual component stain-removing agents alone. Moreover, the combination of stain-removing agents enables reduction of the amount of each of the stain-removing agents in the composition, avoiding unpleasant tastes and mouthfeel. Polyphosphates are one group of agents suitable for use in the present invention as chelators. Chelators are capable of strongly binding with metal ions, such as calcium. For example, chelating agents are able to complex calcium found in the cell walls of bacteria, a major component of plaque. Chelating agents can also disrupt plaque by removing calcium from the calcium bridges which help hold the plaque matrix together.

In some embodiments, stain-removing oral compositions of the present invention include a hydroxy fatty acid salt and an abrasive agent. This combination of stain-removing agents improves stain-removing activity over the activity of the individual component stain-removing agents alone. Furthermore, the combination of stain-removing agents enables reduction of the amount of each of the stain-removing agents in the composition, avoiding unpleasant tastes and mouthfeel.

In some embodiments, the stain-removing oral compositions according to the present invention include the combination of a hydroxy fatty acid salt, a chelating agent and an abrasive agent. This combination of stain-removing agents significantly improves stain-removing activity over the activity of the individual components stain-removing agents alone, and also enables reduction of the amount of each of the stain-removing agents in the composition. In particular, matured stains can be mechanically abraded through the use of the abrasive. Brushing, scrubbing, polishing, or chewing can compliment successful stain removal. The hydroxy fatty acid salt and the chelating agent (e.g., a polyphosphate) serve as surface-active agents. Both of these actives help to soften the pellicle film on the teeth and have the ability to penetrate the stain matrix and facilitate its removal. Moreover, a hydroxy fatty acid salt is a film-forming surfactant, which is capable of binding calcium because of its hydroxyl group. This allows it to have a better affinity for the tooth surface, to penetrate the stain/plaque faster and to form a film for preventing stain formation.

The term "stain-removing effective amount" as used herein is an amount of the combination of stain-removing agent(s) disclosed herein that is sufficient to prevent, eliminate, or at least reduce, the presence of stains on dental surfaces in warm-blooded animals including humans, but low enough to avoid any undesirable side effects. This stain-removing effective amount of the combination of stain-removing agent(s) of the present invention may vary with the type and extent of the particular stain, the age and physical condition of the warm-blooded animal, including humans being treated, the duration of treatment, the nature of concurrent therapy, the specific stain-removing agent employed, and the particular carrier from which the stain-removing agent is applied.

The concentration of the stain-removing agents in the composition of the present invention depends on the type of composition (e.g., toothpaste, mouthwash and rinse, lozenge, chewing gum, confectionary, and the like) used to apply the stain-removing agents to the dental surfaces, due to the differences in the efficiency of the compositions contacting the teeth and due also to the effective amount of the composition generally used. The concentration may also depend on the levels of the stains present.

Except as otherwise noted, the amount of the ingredients incorporated into the compositions according to the present invention is designated as percentage by weight based on the total weight of the composition.

As described above, a stain-removing oral composition of the present invention can be a gum composition, such as chewing gum composition. The chewing gum compositions of the present invention may be coated or uncoated, and be in the form of slabs, sticks, pellets, balls and the like. The composition of the different forms of the chewing gum compositions will be similar but may vary with regard to the ratio of the ingredients. For example, coated gum compositions may contain a lower percentage of softeners. Pellets and balls may have a chewing gum core, which has been coated with either a sugar solution or a sugarless solution to create the hard shell. Slabs and sticks are usually formulated to be softer in texture than the chewing gum core. In some cases the hydroxy fatty acid salt may have a softening effect on the gum base. In order to adjust for any potential undesirable softening effect that the surfactant active (e.g., hydroxy fatty acid salt) may have on the gum base, it may be beneficial to formulate a slab or stick gum having a firmer texture than usual (i.e., use less conventional softener than is typically employed).

Center-filled gum is another common gum form. The gum portion has a similar composition and mode of manufacture to that described above. However, the center-fill is typically an aqueous liquid or gel, which is injected into the center of the gum during processing. The stain-removing agent(s) could optionally be incorporated into the center-fill during manufacture of the fill, incorporated directly into the chewing gum portion of the total gum composition, or both. The center-filled gum may also be optionally coated and may be prepared in various forms, such as in the form of a lollipop.

In some embodiments of the present invention, a coated gum may be formed, wherein the stain-removing agent(s) is in at least one of the core or the coating. For example, in some embodiments, an abrasive agent is incorporated into the coating, and the surface actives (i.e., surfactant and chelating agent) are incorporated into the gum base. By providing the abrasive in the coating, the stain is first mechanically abraded by the abrasive in combination with chewing, which requires close contact with the teeth. In particular, the abrasive tends to have a short time before it goes into solution. Whereas the abrasive continues to have a chemical effect in removing the stain after it is released from the coating into the saliva, it may be advantageous to enhance the mechanical abrasion initially by providing it in the coating layer. Furthermore, the coating provides another effective vehicle for delivering the hydroxy fatty acid salt and/or the chelating agent.

It is also well within the contemplation of the present invention that the stain-removing agent(s) can be incorporated into the gum base. The gum base provides another effective vehicle for delivering stain-removing agent(s), such as the abrasives and the surface-active agents because it permits protracted contact of the stain-removing agents to the teeth. For example, the abrasive, surfactant and chelating agent can chemically remove the stain once released from the gum base and/or coating into saliva.

Chewing gum compositions of the present invention may include a gum base and most of the other typical chewing composition components, such as sweeteners, softeners, flavorants and the like. At least one stain-removing hydroxy fatty acid salt is employed in the inventive gum compositions.

In accordance with one aspect of a gum composition of the present invention, the stain-removing-hydroxy fatty acid salt may be added during the manufacture of the gum composition, that is, with the sweeteners, flavorants and the like. In another aspect of the present invention, the hydroxy fatty acid salt may be added as one of the last steps in the formation of the gum composition. This process allows for the surfactant to be incorporated into the gum composition without materially binding it therein such as may occur if the stain-removing agent is mixed directly with the gum base. Thus, although the surfactant is quite soluble in saliva and can be effectively released from the gum base, by only loosely containing it within the gum composition, it is anticipated that the surfactant can be even more effectively released therefrom during a typical chewing operation. Moreover, the surfactant may be encapsulated or absorbed on a particulate substrate (for example, in a sugar alcohol, wax or polymer such as polyvinyl acetate) to further facilitate delivery, if desired.

Surfactants

The oral compositions of the present invention may include desirable stain-removing agent(s) as provided herein. For example, the composition may include anionic surfactants and nonionic surfactants or mixtures thereof. Anionic surfactants useful herein include water-soluble salts of hydroxy fatty acids having from 14 to 25 carbon atoms. In some embodiments, the salt includes a metal ion that can be a divalent metal ion or a monovalent metal ion. For example, the metal ion can be selected from sodium, potassium, calcium, magnesium and combinations thereof.

Suitable examples of hydroxy fatty acid salts include salts of higher fatty acids, such as ricinoleic acid, castor oil and ergot oil. Ricinoleic acid accounts for about 90% of the triglyceride fatty acids of castor oil, and up to about 40% of the glyceride fatty acids of ergot oil. Other suitable hydroxy fatty acid salts include, but are not limited to, those derived from the following: lesquerolic acid, densipolic acid, auricolic acid and β-dimorphecolic acid. Combinations of hydroxy fatty acid salts may also be employed.

The water-soluble salts of hydroxy fatty acids may be derived from naturally occurring fatty acids having at least one hydroxyl functionality, such as ricinoleic acid. Furthermore, the surfactants employed in the present invention or the fatty acids from which they are derived may be chemically or enzymatically modified so as to contain at least one hydroxyl functionality.

The fatty acid salts may be derived from fatty acids found, for example, in animals, plants or bacteria. The polar —COOH group on short-chain fatty acids (e.g., 2-4 carbon atoms) and even medium-chain (e.g., 6 to 10 carbon atoms) is typically enough to make them soluble in water. However, as chain length increases (e.g., from 14 to 25 carbons), the fatty acid type becomes progressively less water soluble and tends to take on oily or fatty characteristics. The presence of a hydroxy group on long-chain fatty acids increases water solubility. Therefore, Applicants have found that water-soluble salts of hydroxy fatty acids having from 14 to 25 carbon atoms are useful in the compositions of the present invention. In particular, the water solubility of a hydroxy fatty acid salt allows it to solubilize an established stain into the saliva and loosens it so that it can be easily removed by chewing, brushing or saliva.

In some embodiments, the inventive oral compositions can include a hydroxy fatty acid salt in combination with other anionic or nonionic surfactants. For example, other suitable surfactants may include the following anionic or non-ionic surfactants: sulfated butyl oleate, medium and long chain fatty acid esters, sodium oleate, salts of fumaric acid, potassium glomate, organic acid esters of mono- and diglycerides, stearyl monoglyceridyl citrate, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated mono- and diglycerides, sorbitan monostearate, calcium stearyl-2-lactylate, sodium stearyl lactylate, lactylated fatty acid esters of glycerol and propylene glycol, glycerol-lactoesters of $C_8$-$C_{24}$ fatty acids, polyglycerol esters of $C_8$-$C_{24}$ fatty acids, propylene glycol alginate, sucrose $C_8$-$C_{24}$ fatty acid esters, diacetyl tartaric and citric acid esters of mono- and diglycerides, triacetin, sarcosinate surfactants, isethionate surfactants, tautate surfactants, pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures thereof.

The surfactant (e.g., sodium ricinoleate), alone or in combination with other surfactants, may be present in oral compositions of the present invention in concentrations of about 0.001% to about 20% by weight of the total composition. In some embodiments, the surfactant may be present at about 0.05 to about 10% by weight of the total composition. Moreover, in some embodiments, the surfactant may be present in amounts of about 0.05 to about 2% by weight of the total composition.

Chelating Agents

As described above, the oral compositions of the present invention may optionally include chelating agents. Chelating agents strongly interact with metal ions, such as the calcium found in the cell walls of mouth bacteria. Chelating agents can also disrupt plaque by removing calcium from the calcium bridges which help hold this biomass intact.

One group of agents suitable for use as chelating agents in the compositions of the present invention are polyphosphates.

In some embodiments, the chelating agent is a phosphate salt selected from the following: pyrophosphates, triphosphates, polyphosphates, polyphosphonates and combinations thereof. The chelating agent can be a dialkali metal pyrophosphate salt, a tetra alkali polyphosphate salt or a combination thereof. For example, in some embodiments, the chelating agent can be selected from the following: tetrasodium pyrophosphate, tetrapotassium pyrophosphate, sodium tripolyphosphate and combinations of these. Other chelating agents that can be employed in the compositions of the present invention may include tartaric acid and salts thereof, citric acid and alkali metal citrates and mixtures thereof.

In some embodiments, the chelating agent is present in amounts of about 0.001 to about 5% by weight of the inventive oral composition. Furthermore, in some embodiments, the chelating agent is present in amounts of about 0.5 to about 3% by weight of the oral composition.

Abrasive Agent

In some embodiments, the oral compositions of the present invention include an abrasive agent. Suitable abrasives include silicas, aluminas, phosphates, carbonates and combinations thereof. In some embodiments, the abrasive agent is a silica selected from: precipitated silica, silica gels and combinations thereof. Moreover, in some embodiments the abrasive agent is selected from the following: calcium carbonate, sodium bicarbonate, sodium metaphosphate, potassium metaphosphate, tricalcium phosphate, dehydrated dicalcium phosphate and combinations thereof.

The abrasive polishing material contemplated for use in the compositions of the present invention can be any material which does not excessively abrade dentin. However, silica dental abrasives have unique benefits of exceptional dental cleaning and polishing performance without unduly abrading tooth enamel or dentin.

The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in U.S. Pat. No. 3,538,230 to Pader, et al. and U.S. Pat. No. 3,862,307 to DiGiulio, both incorporated herein by reference in their entirety. Preferred are the silica xerogels marketed under the trade name "Syloid" by the W.R. Grace & Company, Davison Chemical Division. Also preferred are the precipitated silica materials, such as those marketed by the J.M. Huber Corporation under the trade name "Zeodent", particularly the silica carrying the designation "Zeodent 119". The types of silica dental abrasives useful in the present invention are described in detail in U.S. Pat. No. 4,340,583 to Wason, incorporated herein by reference in its entirety. Silica abrasives described in U.S. patent application Ser. Nos. 08/434,147 and 08/434,149, both filed May 2, 1995, are also herein incorporated by reference.

In some embodiments, the abrasive is present in amounts from about 0.1 to about 30% by weight of the oral composition. The abrasive agent may be more typically employed in amounts from about 0.5 to about 5% by weight of the total composition. The abrasive in the toothpaste compositions of this invention is generally present at a level of from about 0.5% to about 10% by weight of the composition. Moreover, inventive chewing gum may contain from about 1% to about 6% of abrasive, by weight of the oral composition.

The silica used to prepare a chewing gum composition of the present invention is differentiated by means of its oil absorption value, having oil absorption value of less than 100 cc/100 g, and preferably in the range of from 45 cc/100 g silica to less than 70 cc/100 g silica. Silica particularly useful in the practice of the present invention is marketed under the trade designation SYLODENT XWA GRACE Davison Co., Columbia, DS 21044. An example of such silica is SYLODENT XWA 150, a silica precipitate having a water content of 4.7% by weight averaging from about 7 to about 11 microns in diameter, having an Einlehner Hardness of 5, a BET surface area of 390 m.sup.2/g of silica, an oil absorption of less than 70 cm.sup.3/100 g of silica. This silica exhibits low abrasiveness to tooth enamel.

The silica abrasive can be used as the sole abrasive in preparing a chewing gum of the present invention or in combination with other known abrasives or polishing agents, including calcium carbonate, sodium bicarbonate, sodium metaphosphate, potassium metaphosphate, tricalcium phosphate, dehydrated dicalcium phosphate, or other siliceous materials, or combinations thereof.

In some embodiments, the total quantity of abrasive silica present in a chewing gum composition of the present invention is at a concentration of from about 0.1 to about 20% by weight. Moreover, in some embodiments, the total quantity of abrasive silica present in a chewing gum composition of the present invention is from about 0.5% to about 5% by weight.

Orally Acceptable Carrier

The compositions of the present invention include an orally acceptable carrier, in an appropriate amount to accommodate the other components of the formulation. The term "orally acceptable carrier" refers to a vehicle capable of being mixed with the active components for delivery to the oral cavity for tooth whitening and cleaning purposes, and which will not cause harm to warm-blooded animals, including humans. The orally acceptable carriers further include those components of the composition that are capable of being comingled without interaction in a manner which would substantially reduce the composition's stability and/or efficacy for dental stain-removal in the oral cavity of warm-blooded animals, including humans, in accordance with the compositions and methods of the present invention.

The orally acceptable carriers of the present invention can include one or more compatible solid or liquid filler diluents or encapsulating substances, which are suitable for oral administration. The carriers or excipients employed in the present invention may be in any form appropriate to the mode of delivery, for example, solutions, colloidal dispersions, emulsions, suspensions, rinses, gels, foams, powders, solids, and the like, and can include conventional components of toothpastes (including gels), mouthwashes and rinses, mouth sprays, chewing gums, lozenges, and confectionaries. Carriers suitable for the preparation of compositions of the present invention are well known in the art. Their selection will depend on secondary considerations like taste, cost, shelf stability and the like.

Types of additives or ingredients, which may be included in the present compositions include one or more desirable stain-removing agents as provided herein. The inventive compositions may also include a component selected from the following: elastomers, elastomer solvents, waxes, emulsifiers, plasticizers, softeners, dispersing agents, sweeteners, flavorants, humectants, active agents, cooling agents, warming agents, tooth whitening agents, colorants, bulking agents, fillers and combinations thereof.

In some embodiments, an active agent can be a fluoride compound or an antibacterial compound. For example, a known antibacterial compound is triclosan.

Moreover, in some embodiments a film-forming polymer may be included in the compositions of the present invention.

For example, the film-forming polymer may be a synthetic anionic polymeric polycarboxylate (SAPP), such a PVM/MA copolymer (Gantrez S-97, GAF Corp.). Such polymers are described in U.S. Pat. Nos. 5,334,375 and 5,505,933, which are incorporated by reference herein in their entirety. SAPP's have previously been described as being useful for dentin sensitivity reduction. Moreover, SAPP's have previously been described as antibacterial-enhancing agents, which enhance delivery of an antibacterial agent to oral surfaces, and which enhance the retention of the antibacterial agent on oral surfaces. It is well within the contemplation of the present invention that film-forming polymers, such as PVM/MA copolymer, may be employed in the compositions of the present invention as a means of reducing stain formation.

As described above, in some embodiments, the inventive composition may be a gum composition including a gum base and a surfactant, which comprises a fatty acid salt having at least one hydroxyl functionality. In some embodiments, the surfactant is the hydroxy fatty acid salt of ricinoleic acid.

Gum compositions according to the present invention may further include a chelator, such as a polyphosphate. Suitable examples are the same as those described above.

Moreover, gum compositions of the present invention may include abrasives, suitable examples of which are the same as those described above. For example, in one specific embodiment, the abrasive in the gum is a silica abrasive. A useful silica is one having an oil absorption value of less than 100 cc/100 g silica, and preferably in the range of from 45 cc/100 g silica to less than 70 cc/100 g silica. A suitable silica is sold under the name SYLODENT XWA (Davison Co., Columbia, Md.).

In addition to the hydroxy fatty acid salts, it is also well within the contemplation of the present invention that the inventive gum compositions may further include other anionic or nonionic surfactants. Suitable examples are the same as those described above. These may be included within the gum base, for example.

The gum base may be present in an amount of about 20 to about 40% by weight of the total composition. It may include any component known in the chewing gum art. For example, the gum base may include sweeteners, elastomers, bulking agents, waxes, elastomer solvents, emulsifiers, plasticizers, fillers, mixtures thereof and may include a desirable stain-removing agent(s) as provided herein.

In some embodiments, the gum base may include a suitable sugar bulking agent. For example, the gum base may include a specific polyol composition including at least one polyol which is from about 30% to about 80% by weight of the gum base, and desirably from 50% to about 60%. The polyol composition may include any polyol known in the art including, but not limited to maltitol, sorbitol, erythritol, xylitol, mannitol, isomalt, lactitol and combinations thereof. Lycasin which is a hydrogenated starch hydrolysate including sorbitol and maltitol, may also be used.

Maltitol is a sweet, water-soluble sugar alcohol useful as a bulking agent in the preparation of beverages and foodstuffs and is more fully described in U.S. Pat. No. 3,708,396, which disclosure is incorporated herein by reference. Maltitol is made by hydrogenation of maltose which is the most common reducing disaccharide and is found in starch and other natural products.

The polyol composition which may include one or more different polyols which may be derived from a genetically modified organism ("GMO") or GMO free source. For example, the maltitol may be GMO free maltitol or provided by a hydrogenated starch hydrolysate.

Some embodiments may include a polyol composition including maltitol which has a greater crystalline density than sorbitol. Other polyols which exhibit a greater crystalline density than sorbitol include xylitol and mannitol. Polyols of a greater crystalline density may be useful in center-fill gums. Specifically, a polyol of a greater crystalline density results in a structure with fewer pores, which provides less surface area for potential moisture or fluid migration into the gum region from the liquid-fill.

The polyol composition may also have a sweetness of greater than about 50% of the sweetness of sucrose. Also, the polyol composition of some embodiments has a solubility of less than 67% by weight at 25° C. and greater than about 18% by weight at 25° C.

The polyol composition may include particles of a variety of sizes. Specifically, the average particle size of the polyol composition ranges from about 30 microns to about 600 microns, more specifically from about 30 microns to about 200 microns.

The elastomers (rubbers) employed in the gum base will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

The amount of elastomer employed in the gum base may vary depending upon various factors such as the type of gum base used, the consistency of the gum composition desired and the other components used in the composition to make the final chewing gum product. In general, the elastomer will be present in the gum base in an amount from about 10% to about 60% by weight of the gum region, desirably from about 35% to about 40% by weight.

When a wax is present in the gum base, it softens the polymeric elastomer mixture and improves the elasticity of the gum base. The waxes employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other ingredients, such as components selected from elastomer solvents, emulsifiers, plasticizers, fillers, and mixtures thereof.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing any immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the gum base.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include are the hydrogenated vegetable oils and include soybean oil and cottonseed oil which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

Although softeners may be present to modify the texture of the gum composition, they may be present in reduced amounts as compared to typical gum compositions. For example, they may be present from about 0.5 to about 10% by weight based on the total weight of the composition, or they may not be present in the composition, since the surfactant active can act as a softener.

The gum base of this invention may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. Preferably the amount of filler, when used, will be present in an amount from about 15% to about 40%, and desirably from about 20% to about 30%, by weight of the gum base.

A variety of traditional ingredients may be optionally included in the gum base in effective amounts such as coloring agents, antioxidants, preservatives, flavoring agents, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the gum base.

Some embodiments extend to methods of making the gum compositions. The manner in which the gum base components are mixed is not critical and is performed using standard techniques and apparatus known to those skilled in the art. In a typical method, an elastomer is admixed with an elastomer solvent and/or a plasticizer and/or an emulsifier and agitated for a period of from 1 to 30 minutes. The remaining ingredients, such as the low melting point wax, are then admixed, either in bulk or incrementally, while the gum base mixture is blended again for 1 to 30 minutes.

The gum composition may include amounts of conventional additives selected from, but not limited to, the following: sweetening agents (sweeteners), plasticizers, softeners, emulsifiers, waxes, fillers, bulking agents (carriers, extenders, bulk sweeteners), mineral adjuvants, flavoring agents (flavors, flavorings), coloring agents (colorants, colorings), antioxidants, acidulants, thickeners, medicaments, and the like, and mixtures thereof. Some of these additives may serve more than one purpose. For example, in sugarless gum compositions, a sweetener, such as maltitol or other sugar alcohol, may also function as a bulking agent.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants.

In some embodiments, the gum region may also contain a bulking agent. Suitable bulking agents may be water-soluble and include sweetening agents selected from, but not limited to, monosaccharides, disaccharides, polysaccharides, sugar alcohols, and mixtures thereof; randomly bonded glucose polymers such as those polymers distributed under the tradename POLYDEXTROSE by Pfizer, Inc., Groton, Conn.; isomalt (a racemic mixture of alpha-D-glucopyranosyl-1,6-mannitol and alpha-D-glucopyranosyl-1,6-sorbitol manufactured under the tradename PALATINIT by Suddeutsche Zucker), maltodextrins; hydrogenated starch hydrolysates; hydrogenated hexoses; hydrogenated disaccharides;

minerals, such as calcium carbonate, talc, titanium dioxide, dicalcium phosphate; celluloses; and mixtures thereof.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof.

Suitable sugar alcohol bulking agents include sorbitol, xylitol, mannitol, galactitol, maltitol, and mixtures thereof.

Suitable hydrogenated starch hydrolysates include those disclosed in U.S. Pat. Nos. 25,959, 3,356,811, 4,279,931 and various hydrogenated glucose syrups and/or powders which contain sorbitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN, a commercially available product manufactured by Roquette Freres of France, and HYSTAR, a commercially available product manufactured by Lonza, Inc., of Fairlawn, N.J., are also useful.

The sweetening agents used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as dihydrochalcones, monellin, steviosides, glycyrrhizin, dihydroflavenol, and sugar alcohols such as sorbitol, mannitol, maltitol, and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructofuranoside, or 4,1'-dichloro-4,1'-dideoxygalactosucrose; 1',6'-dichloro1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro4,6,1',6'-tetradeoxygalacto-sucrose; and 4,6,1',6'-tetradeoxy-sucrose, and mixtures thereof; and (e) protein based sweeteners such as thaumaoccous danielli (Thaumatin I and II).

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

Desirably, the sweetener is a high intensity sweetener such as aspartame, sucralose, and acesulfame potassium (Ace-K).

In general, an effective amount of sweetener may be utilized to provide the level of sweetness desired, and this amount may vary with the sweetener selected. The amount of sweetener may be present in amounts from about 0.001% to about 3%, by weight of the gum composition, depending upon the sweetener or combination of sweeteners used. The exact range of amounts for each type of sweetener may be selected by those skilled in the art.

The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof.

In some embodiments, the flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well-known.

In some embodiments, the flavoring agents may be used in many distinct physical forms well-known in the art to provide an initial burst of flavor and/or a prolonged sensation of flavor. Without being limited thereto, such physical forms include free forms, such as spray dried, powdered, beaded forms, encapsulated forms, and mixtures thereof.

The amount of flavoring agent employed herein may be a matter of preference subject to such factors as the type of final chewing gum composition, the individual flavor, the gum base employed, and the strength of flavor desired. Thus, the amount of flavoring may be varied in order to obtain the result desired in the final product and such variations are within the capabilities of those skilled in the art without the need for undue experimentation. In gum compositions, the flavoring agent is generally present in amounts from about 0.02% to about 5%, and more specifically from about 0.1% to about 2%, and even more specifically, from about 0.8% to about 1.8%, by weight of the chewing gum composition.

Coloring agents may be used in amounts effective to produce the desired color. The coloring agents may include pigments which may be incorporated in amounts up to about 6%, by weight of the gum composition. For example, titanium dioxide may be incorporated in amounts up to about 2%, and preferably less than about 1%, by weight of the gum composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No.2, which is the disodium salt of 5,5-indigotindisulfonic acid. Similarly, the dye known as F.D.& C. Green No.1 comprises a triphenylmethane dye and is the monosodium salt of 4-[4-(N-ethyl-p-sulfoniumbenzylamino)diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

Suitable oils and fats usable in gum compositions include partially hydrogenated vegetable or animal fats, such as coconut oil, palm kernel oil, beef tallow, and lard, among others. These ingredients when used are generally present in amounts up to about 7%, and preferably up to about 3.5%, by weight of the gum composition.

Some embodiments may include a method for preparing the gum compositions, including both chewing gum and bubble gum compositions. The chewing gum compositions may be prepared using standard techniques and equipment known to those skilled in the art. The apparatus useful in accordance with some embodiments comprises mixing and heating apparatus well known in the chewing gum manufacturing arts, and therefore the selection of the specific apparatus will be apparent to the artisan.

In some embodiments, a method of preparing a stain-removing gum composition includes heating a gum base to soften the base and then mixing the softened gum base with a fatty acid salt having at least one hydroxyl functionality so as to obtain a substantially homogeneous mixture. The method further includes cooling the mixture and forming the cooled mixture into individual gum pieces. The hydroxy fatty acid salt may be a salt of ricinoleic acid, such as sodium ricinoleate. Further ingredients may be mixed into the softened gum base. For example, one or more of the following may typically be added: bulking agent, filler, humectant, flavorant, colorant, dispersing agent, softener, plasticizer, preservative, warming agent, cooling agent, tooth whitening agent and sweetener.

In some embodiments, gum pieces may be coated with an aqueous coating composition, which may be applied by any method known in the art. The coating composition may be present in an amount from about 25% to about 35% by weight of the total gum piece, more specifically about 30% by weight of the gum piece.

The outer coating may be hard or crunchy. Typically, the outer coating may include sorbitol, maltitol, xylitol, isomalt, and other crystallizable polyols; sucrose may also be used. Flavors may also be added to yield unique product characteristics. Moreover, the outer coating may include one or more of the stain-removing agents provided herein.

The coating, if present, may include several opaque layers, such that the chewing gum composition is not visible through the coating itself, which can optionally be covered with a further one or more transparent layers for aesthetic, textural and protective purposes. The outer coating may also contain small amounts of water and gum arabic. The coating can be further coated with wax. The coating may be applied in a conventional manner by successive applications of a coating solution, with drying in between each coat. As the coating dries it usually becomes opaque and is usually white, though other colorants may be added. A polyol coating can be further coated with wax. The coating can further include colored flakes or speckles.

If the composition comprises a coating, it is possible that one or more oral care actives can be dispersed throughout the coating. This may be preferred if one or more oral care actives is incompatible in a single phase composition with another of the actives.

Moreover, it is well within the contemplation of the present invention that providing one or more of the stain-removing agents in the coating can enhance the stain-removing efficacy of the total composition. For example, as described above, the mechanical abrasion may be initially enhanced by providing the abrasive in the coating layer. Chemical cleaning effects are also enhanced as a result.

Furthermore, the hydroxy fatty acid salt can be included in one or more of the chewing gum regions such as the coating, the gum base or both. Additionally, the hydroxy fatty acid salt can be added at different stages of the manufacture, alone or as a premix with other components. For example, in some embodiments, the method for preparing a stain-removing gum composition includes heating a gum base to soften the base; and mixing the softened gum base with at least one of the following: elastomer, wax, emulsifier, bulking agent, filler, humectant, flavorant, colorant, dispersing agent, softener, plasticizer, preservative, warming agent, cooling agent, tooth whitening agent and sweetener to obtain a substantially homogeneous mixture. The method also involves cooling the mixture; forming the cooled mixture into individual gum pieces; and coating the gum pieces with an aqueous coating solution including a fatty acid salt having at least one hydroxyl functionality. The hydroxy fatty acid salt may be a salt of ricinoleic acid. One or more other ingredients may be included in the coating composition, such as including, but not limited to, the following: gum arabic, flavorant, colorant, sweetener, bulking agent, filler, anti-adherent compound, dispersing agent, moisture absorbing compound, warming agent, cooling agent and film-forming agent.

The coating may be formulated to assist with increasing the thermal stability of the gum piece and preventing leaking of a liquid fill if the gum product is a center-filled gum. In some embodiments, the coating may include a gelatin composition. The gelatin composition may be added as a 40% by weight solution and may be present in the coating composition from about 5% to about 10% by weight of the coating composition, and more specifically about 7% to about 8%. The gel strength of the gelatin may be from about 130 bloom to about 250 bloom.

Additives, such as physiological cooling agents, throat-soothing agents, spices, warming agents, tooth-whitening agents, breath-freshening agents, vitamins minerals, caffeine, drugs and other actives may be included in any or all portions of the chewing gum composition. Such components may be used in amounts sufficient to achieve their intended effects.

With respect to cooling agents, a variety of well known cooling agents may be employed. For example, among the useful cooling agents are included menthol, xylitol, menthane, menthone, menthyl acetate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol, among others. These and other suitable cooling agents are further described in the following U.S. patents, all of which are incorporated in their entirety by reference hereto: U.S. Pat. Nos. 4,230,688 and 4,032,661 to Rowsell et al.; U.S. Pat. No. 4,459,425 to Amano et al.; U.S. Pat. No. 4,136,163 to Watson et al.; and U.S. Pat. No. 5,266,592 to Grub et al. These cooling agents may be present in one or more of the outer gum coatings, the gum region surrounding the liquid fill, the liquid fill per se, or in any combination of those three gum areas. Cooling agents, when used in the outer coating composition for the gum, are generally present in amount of 0.01% to about 1.0%. When used in the other portions of the gum, such as the gum region or the center fill, they may be present in amounts of about 0.001 to about 10% by weight of the total chewing gum piece.

Warming components may be selected from a wide variety of compounds known to provide the sensory signal of warming to the user. These compounds offer the perceived sensation of warmth, particularly in the oral cavity, and often enhance the perception of flavors, sweeteners and other organoleptic components. Among the useful warming compounds included are vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamyleather, vanillyl alcohol n-hexyleather, vanillyl alcohol methylether, vanillyl alcohol ethyleather, gingerol, shogaol, paradol, zingerone, capsaicin, dihydrocapsaicin, nordihydrocapsaicin, homocapsaicin, homodihydrocapsaicin, ethanol, isopropol alcohol, iso-amylalcohol, benzyl alcohol, glycerine, and combinations thereof.

The features and advantages of the present invention are more fully shown by the following examples which are provided for purposes of illustration, and are not to be construed as limiting the invention in any way.

EXAMPLES

Example 1

Uncoated Chewing Gum Compositions

TABLE 1

Chewing Gum Ingredients

| | Chewing Gum Prototypes | | | | |
|---|---|---|---|---|---|
| Material Description | A % Wt. | B % Wt. | C % Wt. | D % Wt. | E % Wt. |
| Gum Base | 24.00 | 24.00 | 24.00 | 24.00 | 24.00 |
| Sorbitol | QS | QS | QS | QS | QS |
| Glycerine | 4.50 | 4.50 | 4.50 | 4.50 | 4.50 |
| Flavor Blend | 2.10 | 2.10 | 2.10 | 2.10 | 2.10 |
| Ace - K | 0.05 | 0.05 | 0.05 | 0.05 | 0.05 |
| APM Free | 0.21 | 0.21 | 0.21 | 0.21 | 0.21 |
| Gum Arabic | 1.21 | 1.21 | 1.21 | 1.21 | 1.21 |
| Silicon dioxide | 0.00 | 0.00 | 2.00 | 0.00 | 2.00 |
| Sodium tripolyphosphate | 0.00 | 0.50 | 1.00 | 0.50 | 0.50 |
| Sodium Ricinoleate | 0.00 | 0.00 | 0.00 | 0.50 | 0.25 |
| Sodium Stearate | 0.50 | 0.50 | 0.50 | 0.00 | 0.00 |
| Total | 100.00 | 100.00 | 100.00 | 100.00 | 100.00 |

Experimental

Chewing gum compositions A, B, C, D and E shown in Table 1 above and Table 2 below were prepared by conventional methods. Compositions A, B and C are comparative compositions; and compositions D and E are compositions of the present invention. The method of preparing the compositions involved heating a gum base sufficiently to soften the base without adversely affecting the physical and chemical make-up of the base. The molten gum base and fillers were then added to the mixing kettle. The sugar alcohols, glycerin, flavor, sweeteners, chelating agent, abrasive and surfactant (sodium ricinoleate or sodium stearate) were added with mixing to obtain a substantially homogeneous mixture, with the surfactant component added last. The mixture was then discharged from the mixing kettle and rolled and scored into a desired piece by conventional techniques.

To evaluate the whitening efficacy of Chewing Gums A, B, C, D and E, a mechanical instrument, which was developed by Kleber et al.[1] to simulate the human mastication of chewing gum, was used. For testing, a specimen block with one enamel square was placed in both the upper and lower tooth holders of the instrument. 15 ml of freshly prepared modified artificial human saliva[2] (no amino acid was added) was placed in the reservoir and approximately 3 grams of the test chewing gum (i.e. 2 pellets) was placed between the repositioning paddles directly over the lower tooth specimens. Then the mastication motor was started and the chewing gums were chewed for 60 minutes.

[1] Kleber C J, Schimmele R G, Putt M S, Muhler J c: A mastication device designed for the evaluation of chewing gums. J. Dent Res 60:109-114, 1981.
[2] Shellis R P, 1978. A synthetic saliva for cultural studies of dental plaque. Arch. Oral Biol. 23, 485-489.

Stained bovine teeth were prepared by Indiana-Purdue University. The average L*a*b* color scores for the extrinsic stain on the teeth at baseline were well balanced for each color factor before treatment. All bovine teeth used in this experiment had a value of ΔE<25.

Squares of dental enamel 4 mm on a side were cut, using a diamond cutting disk, from bovine permanent incisors. Using a mold, four of the enamel squares were embedded in clear polyester casting resin to provide 1.5 cm square blocks with the labial surfaces exposed. The top surface of the polyester blocks were ground flush with the leveled labial surfaces of the enamel squares by means of a dental model trimmer. The surface was then smoothed by hand-sanding on 400 grit emery paper using water as the lubricant until all grinding marks were removed. Finally, the top surface of the blocks was hand-polished to a mirror finish using a water slurry of GK1072 calcined kaolin (median particle size=1.2 microns) on a cotton cloth. The finished specimens were examined under a dissecting microscope and discarded if surface imperfections were observed.

In order to render the polished tooth surfaces more similar to natural teeth and promote the formation of stain on the enamel, the specimens were etched for 60 seconds in 0.2 M HCl followed by a final etch with 1% phytic acid for 60 seconds. Then the specimens were rinsed with deionized water and attached to the staining apparatus.

The tooth staining apparatus was designed to provide alternate immersion into the staining broth and air-drying of the specimens. The apparatus consisted of an aluminum platform base which supported a Teflon rod (¾-inch in diameter) connected to an electric motor, which by means of a speed reduction box, rotated the rod at a constant rate of 1.5 rpm. Threaded screw holes were spaced at regular intervals along the length of the rod. The tooth specimens were attached to the rod by first gluing the head of a plastic screw to the back of the specimen, then screwing the tooth onto the rod. Beneath the rod was a removable 300 ml capacity trough which held the tooth staining broth.

The staining broth was prepared by adding 1.02 g of instant coffee, 1.02 g of instant tea, and 0.75 g of gastric mucin to 250 ml of sterilized trypticase soy broth. Approximately 50 ml of a 24-hour stain-promoting *Micrococcus luteus* culture was also added to the stain broth. The apparatus, with the enamel specimens attached and the staining broth in the trough, was then placed in an incubator at 37° C. with the specimens rotating continuously through the staining broth and air. The staining broth was replaced once every 24 hours for ten consecutive days. With each broth change, the trough and specimens were rinsed and tooth brushed with deionized water to remove any loose deposits. On the eleventh day, the staining broth was modified by the addition of 0.03 g of $FeCl_3 6H_2O$, and this was continued with daily broth changes until the stain on the specimens was sufficiently dark (L*<25). Then, the specimens were removed from the staining broth, brushed thoroughly with deionized water, and refrigerated in a humidor until used.

Procedures

In preparation for treatment, the baseline L*a*b* stain scores of the tooth specimens were determined and used to stratify the teeth into balanced groups of 8 specimens each. A mechanical instrument with a flow system to simulate the human mastication was used to treat the tooth specimens with the test chewing gum. For testing, a specimen block with enamel squares was placed in both the upper and lower tooth holders of the instrument.

An artificial saliva (pH 7.3) was placed in the reservoir. Approximately 1.5 grams of test chewing gum (i.e. 2 tablets) was placed between the repositioning paddles directly over the lower tooth specimen. Then the mastication motor was started and the two specimen blocks with the enamel squares were treated with the chewing gums for 5 minutes. This treatment procedure was repeated for 12 consecutive times (a total of 60 minutes of treatment) in order to simulate 4 times/day usage for 3 days. Fresh gums and artificial saliva were used for each 5-minute treatment period. Following the 12$^{th}$ treatments, the specimens were rinsed, allowed to dry for 30 minutes, and color reading made. After the final stain measurements, the specimens were pumiced using a dental hand piece in order to clean all residual stain off of the teeth, then color readings were taken again. This final procedure provided a value for each specimen that represented the maximum amount of stain that potentially could be removed by the test chewing gum or the saliva.

The color of the extrinsic stain on the bovine teeth was measured by taking diffuse reflectance absorbance readings with a Minolta spectrophotometer. Absorbance measurement over the entire visible color spectrum were obtained using the CIELAB color scale. This scale quantifies color according to 3 parameters, L* (lightness-darkness scale); a* (red-green chroma); and b* (yellow-blue chroma). In order to obtain reproducible readings, the stained enamel specimens were allowed to air-dry at room temperature for 60 minutes before measurements were made. Measurements were conducted by aligning the center of the 4 mm square segment of stained enamel directly over the 3 mm diameter targeting aperture of the Minolta spectrophotometer. An average of 3 absorbance readings using the L*a*b* scale were taken for each specimen.

The overall change in the color of the stained teeth was calculated using the CIELAB equation $\Delta E=[(\Delta L^*)^2+(\Delta a^*)^2+(\Delta b^*)^2]^{1/2}$. The individual components of the L*a*b* scale represent the specific changes in the whiteness (L*), red-green color (a*), and yellow-blue color (b*). The $\Delta E$ (i.e., dE) value for each composition tested is shown in Table 2 below, and summarizes the overall change for each color factor ($\Delta L^*$, $\Delta a^*$, and $\Delta b^*$). This value represents the ability of a test chewing gum to remove stain and whiten teeth, wherein the greater the number, the better its ability to remove stains and whiten teeth.

TABLE 2

Results

| Prototype | | dE |
|---|---|---|
| A | Sodium Stearate 0.5% | 3.3 |
| B | Sodium Stearate 0.5%, STP 0.5% | 3.9 |
| C | Sodium Stearate 0.5%, STP 1.0%, Silica 2% | 5.3 |
| D | Sodium Ricinoleate 0.5%, STP 0.5% | 6.7 |
| E | Sodium Ricinoleate 0.16%, STP 0.5%, Silica 2% | 7.1 |

As shown in Table 2, Inventive Compositions D and E were able to remove stains and whiten teeth better than the comparative Compositions A, B and C.

Example 2

Coated Chewing Gum Composition—Surfactant in the Coat

TABLE 3

| Ingredient | Composition F (Wt. %) |
|---|---|
| Core Gum | |
| Gum Base | 26.2500 |
| Atomite (Filler) | 3.7500 |
| Sorbitol | 32.3583 |
| Mannitol | 7.5000 |
| Flavorant | 2.8075 |
| Glycerin | 1.0000 |

TABLE 3-continued

| Ingredient | Composition F (Wt. %) |
|---|---|
| High Intensity Sweetener | 0.7875 |
| Sodium tripolyphosphate | 0.5000 |
| Silicon dioxide | 0.5000 |
| Coat | |
| Maltitol | 22.1228 |
| Ace-K | 0.0350 |
| Flavorant | 0.3430 |
| Gum Arabic | 1.1678 |
| Titanium Dioxide | 0.1780 |
| Candelilla Wax | 0.0334 |
| Sodium ricinoleate | 0.6667 |
| TOTAL | 100.0000 |

In the present example, the hydroxy fatty acid surfactant (sodium ricinoleate) is in the coat. An inventive gum composition is prepared by conventional methods to form Composition F in Table 3. Briefly, a gum base is softened with heating. The molten gum base and filler are added to the mixing kettle and mixing is commenced. The sugar alcohols, glycerin, chelating agent (sodium tripolyphosphate), abrasive agent (silicon dioxide), flavors and high intensity sweetener mixture, are added in portions to obtain a substantially homogeneous mixture. The mixture is then discharged from the mixing kettle, and formed into cores by conventional techniques.

The cores are placed into a coating pan and broken into individual pieces as necessary. A sugarless solution containing 70% by weight of maltitol, as well as titanium dioxide, gum arabic and water is heated to between 70° C. and 80° C. The solution is sprayed onto the gum core pieces in layers and allowed to dry between sprays while the coating pan is continually rotating to ensure a smooth even coat of the gum cores.

The coating is built up to about 8% by weight of the final pellet weight. Ace-K is then added and then covered with another layer of the above-mentioned coating solution and then allowed to dry.

After the high intensity sweetener layer is dried, sodium ricinoleate and a flavorant are added in alternating layers until all of the respective materials are added with each layer being allowed to dry before the next layer is applied. The coating process is continued with the coating solution until the coat comprises 24% by weight of the final pellet weight.

The coating is then topped with a conventional finishing solution until a shell weight of 25% by weight is obtained. The pellets are then polished in a polishing pan with candelilla wax in a conventional manner.

Example 3

Coated Chewing Gum Composition—Abrasive in the Coat

TABLE 4

| Ingredient | Composition G (Wt. %) |
|---|---|
| Core Gum | |
| Gum Base | 26.2500 |
| Atomite (Filler) | 3.7500 |
| Sorbitol | 32.3583 |

TABLE 4-continued

| Ingredient | Composition G (Wt. %) |
|---|---|
| Mannitol | 7.5000 |
| Flavorant | 2.8075 |
| Glycerin | 1.0000 |
| High Intensity Sweetener | 0.7875 |
| Sodium tripolyphosphate | 0.5000 |
| Sodium ricinoleate | 0.5000 |
| Coat | |
| Maltitol | 22.2895 |
| Acesulfame-K (Ace-K) | 0.0350 |
| Flavorant | 0.3430 |
| Gum Arabic | 1.1678 |
| Titanium Dioxide | 0.1780 |
| Candelilla Wax | 0.0334 |
| Silicon dioxide | 0.5000 |
| TOTAL | 100.0000 |

In the present example, the abrasive agent is present in the coat. An inventive gum composition is prepared by conventional methods to form Composition G in Table 4. Briefly, a gum base is softened with heating. The molten gum base and filler are added to the mixing kettle and mixing is commenced. The sugar alcohols, glycerin, chelating agent (sodium tripolyphosphate), surfactant (hydroxy fatty acid salt), flavors and high intensity sweetener mixture are added in portions to obtain a substantially homogeneous mixture. The mixture is then discharged from the mixing kettle, and formed into cores by conventional techniques.

The cores are placed into a coating pan and broken into individual pieces as necessary. A sugarless solution containing 70% by weight of maltitol, as well as titanium dioxide, gum arabic and water is heated to between 70° C. and 80° C. The solution is sprayed onto the gum core pieces in layers and allowed to dry between sprays while the coating pan is continually rotating to ensure a smooth even coat of the gum cores.

The coating is built up to about 8% by weight of the final pellet weight. Ace-K is then added and then covered with another layer of the above-mentioned coating solution and then allowed to dry.

After the high intensity sweetener layer is dried, the abrasive agent (silicon dioxide) and a flavorant are added in alternating layers until all of the respective materials are added with each layer being allowed to dry before the next layer is applied. The coating process is continued with the coating solution until the coat comprises 24% by weight of the final pellet weight.

The coating is then topped with a conventional finishing solution until a shell weight of 25% by weight is obtained. The pellets are then polished in a polishing pan with candelilla wax in a conventional manner.

Example 4

Pressed Mint Products

A composition for forming a pressed mint product in accordance with the present invention is prepared in the following manner.

Sorbitol at 97.0% by weight, 0.5% by weight of silicon dioxide, 0.5% of sodium tripolyphosphate, 0.3% by weight of a flavoring agent, and 0.7% of Aspartame are mixed for two minutes in a blender until a substantially homogeneous mixture is obtained. Sodium ricinoleate is then added to the mixture at 0.5% by weight, followed by blending for about four minutes. Magnesium Stearate is then added to the mixture at 0.5% by weight, followed by blending for about three minutes. The resulting mixture is then formed into individual pressed tablets in a conventional manner.

Example 5

Dentifrice Composition of the Present Invention

In some embodiments, a dentifrice composition of the present invention contains the following ingredients, as described below in Table 5.

TABLE 5

| Ingredients | Wt. % |
| --- | --- |
| Sorbitol | 24.0 |
| Glycerine | 15.0 |
| Polyethylene glycol (PEG) 600 | 4.0 |
| Carboxymethyl cellulose | 0.5 |
| Sodium saccharin | 0.4 |
| Sodium fluoride | 0.25 |
| Deionized water | 27.0 |
| Titanium dioxide | 0.5 |
| Sodium benzoate | 0.5 |
| Flavorants | 1.0 |
| Sodium tripolyphosphate | 5.0 |
| Silica microparticles | 20.0 |
| Sodium ricinoleate | 2.0 |
| Colorant | 0.4 |

The jacket temperature of a mixing tank is set to about 150° F. (65° C). The humectants (glycerine, sorbitol, PEG) and water are added to the mixing tank and agitation is started. When the temperature reaches about 120° F. (50° C.), sweetening agents (saccharin), fluoride, chelant (sodium tripolyphosphate), coloring agents (titanium dioxide) and sodium benzoate are added. Thickening agents (carboxymethyl cellulose) are added to the silica abrasive and the resulting mixture is added to the mixing tank with high agitation. The surfactant (sodium ricinoleate) is added to the combination and mixing is continued. The tank is cooled to 120° F. (50° C.) and the flavoring agents are added. Mixing is continued for approximately 5 minutes to yield the final composition.

What is claimed is:

1. A stain-removing oral composition comprising:
    a gum base; and
    a surfactant in an effective amount to remove stains from teeth, wherein the surfactant comprises a free fatty acid salt having at least one hydroxyl functionality, said free hydroxy fatty acid salt having a greater solubility in saliva and less of an affinity for the gum base relative to other fatty acid salts comprising stearic acid and salts thereof, thereby providing an enhanced stain-removing activity relative to said other fatty acid salts;
    wherein said free fatty acid salt having at least one hydroxyl functionality is a salt of ricinoleic acid.

2. The composition of claim 1, wherein the surfactant is present in amounts of about 0.001 to about 20% by weight of the oral composition.

3. The composition of claim 1, wherein the surfactant is present in amounts of about 0.05 to about 10% by weight of the oral composition.

4. The composition of claim 1, wherein the surfactant is present in amounts of about 0.05 to about 2% by weight of the oral composition.

5. The composition of claim 1, wherein the free hydroxyl fatty acid salt includes a metal ion selected from the group consisting of divalent metal ions and monovalent metal ions.

6. The composition of claim 5, wherein the metal ion is selected from the group consisting of sodium, potassium, calcium, magnesium and combinations thereof.

7. The composition of claim 1, further comprising a chelating agent.

8. The composition of claim 7, wherein the chelating agent is a phosphate salt selected from the group consisting of pyrophosphates, triphosphates, polyphosphates, polyphosphonates and combinations thereof.

9. The composition of claim 7, wherein the chelating agent is selected from the group consisting of dialkali metal pyrophosphate salts, tetraalkali polyphosphate salts and combinations thereof.

10. The composition of claim 7, wherein the chelating agent is selected from the group consisting of tetrasodium pyrophosphate, tetrapotassium pyrophosphate, sodium tripolyphosphate and combinations thereof.

11. The composition of claim 7, wherein the chelating agent is present in amounts of about 0.001 to about 5% by weight of the oral composition.

12. The composition of claim 7, wherein the chelating agent is present in amounts of about 0.5 to about 3% by weight of the oral composition.

13. The composition of claim 1, further comprising an abrasive agent.

14. The composition of claim 13, wherein the abrasive agent is selected from the group consisting of silicas, aluminas, phosphates, carbonates and combinations thereof.

15. The composition of claim 13, wherein said abrasive agent is a silica selected from the group consisting of precipitated silica, silica gels and combinations thereof.

16. The composition of claim 13, wherein the abrasive agent is selected from the group consisting of calcium carbonate, sodium bicarbonate, sodium metaphosphate, potassium metaphosphate, tricalcium phosphate, dihydrated dicalcium phosphate and combinations thereof.

17. The composition of claim 13, wherein the abrasive agent is present in amounts from about 0.1 to about 30% by weight of the oral composition.

18. The composition of claim 13, wherein the abrasive agent is present in amounts from about 0.5 to about 5% by weight of the oral composition.

19. The composition of claim 1, wherein the composition comprises a chewing gum base in amounts of about 20 to about 40% by weight of the composition.

20. The composition of claim 1, further comprising an agent selected from the group consisting of elastomers, elastomer solvents, waxes, emulsifiers, plasticizers, softeners, dispersing agents, sweeteners, flavorants, humectants, active agents, cooling agents, warming agents, tooth whitening agents, colorants, bulking agents, fillers and combinations thereof.

21. The composition of claim 20, wherein the agent is a fluoride compound or an antibacterial compound.

22. The composition of claim 1, further comprising a film-forming polymer.

23. The composition of claim 22, wherein the film-forming polymer is an anionic polymeric polycarboxylate.

24. The composition of claim 1, further comprising a component selected from the group consisting of sulfated butyl oleate, medium and long chain fatty acid esters, sodium oleate, salts of fumaric acid, potassium glomate, organic acid esters of mono- and diglycerides, stearyl monoglyceridyl citrate, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated mono- and diglycerides, sorbitan monostearate, calcium stearyl-2-lactylate, sodium stearyl lactylate, lactylated fatty acid esters of glycerol and propylene glycerol, glycerol-lactoesters of $C_8$-$C_{24}$ fatty acids, polyglycerol esters of $C_8$-$C_{24}$ fatty acids, propylene glycol alginate, sucrose $C_8$-$C_{24}$ fatty acid esters, diacetyl tartaric and citric acid esters of mono- and diglycerides, triacetin, sarcosinate surfactants, isethionate surfactants, tautate surfactants, pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures thereof.

25. A stain-removing chewing gum composition comprising:
    (a) a free water-soluble salt of ricinoleic acid, said free salt of ricinoleic acid having a greater solubility in saliva and less of an affinity for the gum base relative to stearic acid and salts thereof, thereby providing an enhanced stain-removing activity relative thereto; and
    (b) a chelating agent.

26. The composition of claim 25, wherein the salt of ricinoleic acid is present in amounts of about 0.001 to about 20% by weight of the chewing gum composition.

27. The composition of claim 25, wherein the salt of ricinoleic acid is present in amounts of about 0.05 to about 10% by weight of the chewing gum composition.

28. The composition of claim 25, wherein the chelating agent is selected from the group consisting of dialkali metal pyrophosphate salts, tetraalkali polyphosphate salts and combinations thereof.

29. The composition of claim 25, wherein the chelating agent is present in amounts of about 0.001 to about 5% by weight of the chewing gum composition.

30. The composition of claim 25, further comprising an abrasive agent selected from the group consisting of precipitated silica, silica gels and combinations thereof.

31. The composition of claim 30, wherein the abrasive agent is present in amounts of about 0.1 to about 20% by weight of the chewing gum composition.

32. A stain-removing chewing gum composition comprising:
    a gum base; and
    a free water-soluble salt of ricinoleic acid, said free salt of ricinoleic acid having a greater solubility in saliva and less of an affinity for the gum base relative to stearic acid and salts thereof, thereby providing an enhanced stain-removing activity relative thereto.

33. The composition of claim 32, wherein the gum base is present in amounts of about 20 to about 40% by weight of the chewing gum composition.

34. The composition of claim 32, wherein the salt of ricinoleic acid is present in amounts of about 0.001 to about 20% by weight of the chewing gum composition.

35. The composition of claim 32, further comprising a chelating agent selected from the group consisting of dialkali metal pyrophosphate salts, tetraalkali polyphosphate salts and combinations thereof.

36. The composition of claim 35, wherein the chelating agent is present in amounts of about 0.001 to about 5% by weight of the chewing gum composition.

37. The composition of claim 32, further comprising an abrasive agent selected from the group consisting of precipitated silica, silica gels and combinations thereof.

38. The composition of claim 37, wherein the abrasive agent is present in amounts of about 0.1 to about 20% by weight of the chewing gum composition.

39. A stain-removing chewing gum composition comprising:
    a gum base;
    a free water-soluble salt of ricinoleic acid, said free salt of ricinoleic acid having a greater solubility in saliva and less of an affinity for the gum base relative to stearic acid and salts thereof, thereby providing an enhanced stain-removing activity relative thereto;
    a chelating agent; and at least one elastomer.

40. The composition of claim 39, wherein the gum base is present in amounts of about 20 to about 40% by weight of the chewing gum composition.

41. The composition of claim 39, wherein the salt of ricinoleic acid is present in amounts of about 0.001 to about 20% by weight of the chewing gum composition.

42. The composition of claim 39, wherein the chelating agent is selected from the group consisting of dialkali metal pyrophosphate salts, tetraalkali polyphosphate salts and combinations thereof.

43. The composition of claim 39, wherein the chelating agent is present in amounts of about 0.001 to about 5% by weight of the chewing gum composition.

44. The composition of claim 39, further comprising an abrasive agent selected from the group consisting of precipitated silica, silica gels and combinations thereof.

45. The composition of claim 39, wherein the abrasive agent is present in amounts of about 0.1 to about 20% by weight of the chewing gum composition.

46. A stain-removing chewing gum composition comprising:
    a gum base;
    a free water-soluble salt of ricinoleic acid, said free salt of ricinoleic acid having a greater solubility in saliva and less of an affinity for the gum base relative to stearic acid and salts thereof, thereby providing an enhanced stain-removing activity relative thereto;
    a chelating agent; and
    an abrasive agent.

47. The composition of claim 46, wherein the gum base is present in amounts of about 20 to about 40% by weight of the chewing gum composition.

48. The composition of claim 46, wherein the salt of ricinoleic acid is present in amounts of about 0.001 to about 20% by weight of the chewing gum composition.

49. The composition of claim 46, wherein the chelating agent is selected from the group consisting of dialkali metal pyrophosphate salts, tetraalkali polyphosphate salts and combinations thereof.

50. The composition of claim 46, wherein the chelating agent is present in amounts of about 0.001 to about 5% by weight of the chewing gum composition.

51. The composition of claim 46, wherein the abrasive agent is selected from the group consisting of precipitated silica, silica gels and combinations thereof.

52. The composition of claim 46, wherein the abrasive agent is present in amounts of about 0.1 to about 20% by weight of the chewing gum composition.

53. A stain-removing chewing gum composition comprising:
    a gum base present in amounts of about 20 to about 40% by weight of the chewing gum composition;

sodium ricinoleate present in amounts of about 0.05 to about 10% by weight of the chewing gum composition, said sodium ricinoleate having a greater solubility in saliva and less of an affinity for the gum base relative to stearic acid and salts thereof, thereby providing an enhanced stain-removing activity relative thereto;

silicon dioxide present in amounts of about 0.1 to about 20% by weight of the chewing gum composition; and sodium tripolyphosphate present in amounts of about 0.1 to about 5% by weight of the chewing gum composition.

* * * * *